United States Patent [19]

Gale et al.

[11] 4,190,642

[45] Feb. 26, 1980

[54] OCULAR THERAPEUTIC SYSTEM FOR DISPENSING A MEDICATION FORMULATION

[75] Inventors: Robert M. Gale, Mt. View; Monique Ben-Dor; Nancy Keller, both of Palo Alto, all of Calif.

[73] Assignee: Alza Corporation, Palo Alto, Calif.

[21] Appl. No.: 38,086

[22] Filed: May 11, 1979

Related U.S. Application Data

[63] Continuation-in-part of Ser. No. 896,720, Apr. 17, 1978.

[51] Int. Cl.² .................. A61K 9/22; A61K 9/24; A61K 9/50; A61K 9/52
[52] U.S. Cl. .................................. 424/19; 128/260
[58] Field of Search ................. 424/19–22; 128/260

[56] References Cited

U.S. PATENT DOCUMENTS

| | | | |
|---|---|---|---|
| 2,478,182 | 8/1949 | Consolazio | 424/22 X |
| 3,247,066 | 4/1966 | Milosovich | 424/19 |
| 3,376,238 | 4/1968 | Gregorian et al. | 260/2.5 |
| 3,618,604 | 11/1971 | Ness | 128/260 |
| 3,710,795 | 1/1973 | Higuchi et al. | 128/260 |
| 3,845,770 | 11/1974 | Theeuwes et al. | 128/260 |
| 3,854,480 | 12/1974 | Zaffaroni | 128/260 |
| 3,868,445 | 2/1975 | Ryde et al. | 424/14 |
| 3,916,899 | 11/1975 | Theewes et al. | 128/260 |
| 3,923,939 | 12/1975 | Baker et al. | 264/49 |
| 3,952,741 | 4/1976 | Baker | 128/260 |
| 3,991,759 | 11/1976 | Urquhart | 128/260 |

OTHER PUBLICATIONS

Ellis and Smith, Handbook of Ocular Therapeutics & Pharmacology 3rd Ed. (1969) C. V. Mosby, St. Louis, Mo. pp. 171, 172, 192, 193.

Physicians' Desk Reference for Ophthalmology, 1976/1977 Ed. p. 85 Medical Economics Co. Oradell, N.J.

T. Narkis et al. J. Applied Polymer Sci. 20: 3431-3436 (1976) "Slow Release of Water–Soluble Salts from Polymers".

*Primary Examiner*—Shep K. Rose
*Attorney, Agent, or Firm*—Paul L. Sabatine; Edward L. Mandell; Thomas E. Ciotti

[57] ABSTRACT

An ocular system is disclosed for dispensing a medication formulation to the eye. The system comprises a formulation consisting of a pilocarpine osmotic solute and an epinephrine osmotic solute dispersed in a polymer such that the formulation is surrounded substantially individually by the polymer. The system, when placed in the eye, dispenses the formulation at a controlled rate over time. A method also is disclosed for the management of intraocular pressure using the ocular system.

11 Claims, 5 Drawing Figures

EFFECT OF EPINEPHRINE SOLUTE DELIVERED SIMULTANEOUSLY WITH PILOCARPINE SOLUTE ON STEADY STATE AQUEOUS HUMOR PILOCARPINE CONCENTRATION

OCULAR THERAPEUTIC SYSTEM FOR DISPENSING A MEDICATION FORMULATION

CROSS-REFERENCE TO COPENDING APPLICATION

This application is a continuation-in-part of U.S. Patent application Ser. No. 896,720, filed on Apr. 17, 1978, which application Ser. No. 896,720 is incorporated herein by reference, and benefit is claimed of its filing date. This application also is copending with U.S. Patent Application Ser. No. 855,605, filed on Nov. 29, 1977 by Michaels and Guillod. This application and the copending applications are assigned to the Alza Corporation of Palo Alto, California.

FIELD OF THE INVENTION

This invention pertains to a novel and useful ocular therapeutic system housing both a pilocarpine osmotically effective solute and an epinephrine osmotically effective solute. The invention also relates to a method for the management of intraocular pressure by dispensing the solutes from the ocular system to an ocular environment.

BACKGROUND OF THE INVENTION

Pilocarpine and epinephrine are indicated for the management of ocular pressure. Pilocarpine, or (3S-cis)-ethyldihydro-4-[(1-methyl-1H-imidazol-5yl)methyl]-2(3H)-furanone, is a parasympathomimetic drug that lowers intraocular pressure by increasing facility of outflow of aqueous humor from the eye. Epinephrine, or 4-[1-hydroxy-2-(methyl-amino)ethyl]-1,2-benzenediol, is a sympathomimetic drug that diminishes intraocular pressure by the dual effects of reducing aqueous secretion and increasing facility of outflow. These two drugs are commonly used in separate solutions for controlling glaucoma, and sometimes they are used in combination in solution for the same therapeutic purpose. See *Handbook of Ocular Therapeutics and Pharmacology*, by Ellis and Smith, 3rd Edition, pages 171, 172, 192 and 193, published 1969 by C. V. Mosby Company, St. Louis, Mo.; and *Physicians' Desk Reference for Ophthalmology*, page 85, 1976/1977 Edition, published by Medical Economics Company, Oradell, N.J.

In either dosage solutions, serious shortcomings are frequently associated with the use of the solutions. For example, solutions require periodic applications at intervals throughout the day and night, and this results in the eye receiving a massive and unpredictable amount of drug(s) at each application. This kind of application results in the level of drugs(s) surging to a peak, followed by a decline in the concentration of the drug(s). Often, the applied drug(s) are washed away by tear fluid leaving the eye without medication(s). Other shortcomings associated with the pulse-dosage patterns of ocular solution therapy are blurred vision attributed to loss of accommodation, possible disruption of the barrier and transport properties of the corneal epithelium, and epithelial damage arising from the presence of acid buffers and/or eyedrop preservatives in the solution(s), as reported in *Invest. Ophthalmol. Visual. Sci.*, Volume 16, No. 10, pages 899 to 911, 1977. Such eyedrop formulation components are not required for the functioning of the described invention.

In the light of the above presentation, it is immediately evident a long-felt need exists for an ocular system for dispensing pilocarpine and epinephrine to the eye substantially free of the tribulations associated with the prior art dosage forms. The critical need exists for a system that can dispense both pilocarpine and epinehprine in therapeutically effective amounts from the same system for the intended benefits of the drug(s). Particularly, the want persists for a system that can house the two structurally and biologically active different drugs without any interaction, and with the drugs in the system combined and available for immediate and future in vivo use at therapeutically effective rates. It will be appreciated by those versed in the medical and dispensing arts, that if the system is provided that can dispense simultaneously pilocarpine and epinephrine for the management of intraocular pressure, such a system would have a definite use and represents a substantial contribution to the arts. Likewise, it will be further appreciated by those versed in the arts, that if an ocular therapeutic system is made available for delivery of these drugs simultaneously for the management of glaucoma, such a system would have a positive value and represent an unexpected advancement in the field of ocular pharmacology.

OBJECTS OF THE INVENTION

Accordingly, it is an immediate object of the invention to provide a novel and useful ocular therapeutic system that delivers from the same system a pilocarpine therapeutically effective solute and an epinephrine therapeutically effective solute useful for the management of intraocular pressure.

Another object of the invention is to provide an ocular therapeutic system for dispensing the two pharmacologically different drugs, pilocarpine solute and epinephrine solute, at a controlled rate, in combination, for use as anti-glaucoma medications.

Yet another object of the invention is to provide an ocular insert that embraces an osmotic structure, and releases in combination pilocarpine solute and epinephrine solute at osmotically controlled rates.

Still another object of the invention is to provide an ocular insert consisting essentially of pilocarpine solute and epinephrine solute, which solutes possess different physical and chemical properties, yet can be released from the insert at controlled useful rates over time.

These objects, as well as other objects, features and advantages of the invention will become more readily apparent from the following detailed description, the drawings, and the accompanying claims.

SUMMARY OF THE INVENTION

This invention concerns an ocular insert useful for the management of glaucoma. The insert houses and dispenses in combination the two physically and chemically distinct drugs, pilocarpine solute and epinephrine solute, that exhibit both osmotically and biologically different properties, yet they are dispensed from the system at controlled and beneficial rates over a prolonged period of time. The invention also pertains to a method of using the insert, and for dispensing the combination for treating glaucoma.

BRIEF DESCRIPTION OF THE DRAWINGS

In the drawings, which are not drawn to scale, but are set forth to illustrate the invention, the FIGS. are as follows.

In the drawings and specification, like parts in related FIGS. are identified by like numbers. The terms appearing earlier in the specification and in the description of the drawings as well as embodiments thereof, are further described elsewhere in the disclosure.

DETAILED DESCRIPTION OF THE DRAWINGS

Figure 1:
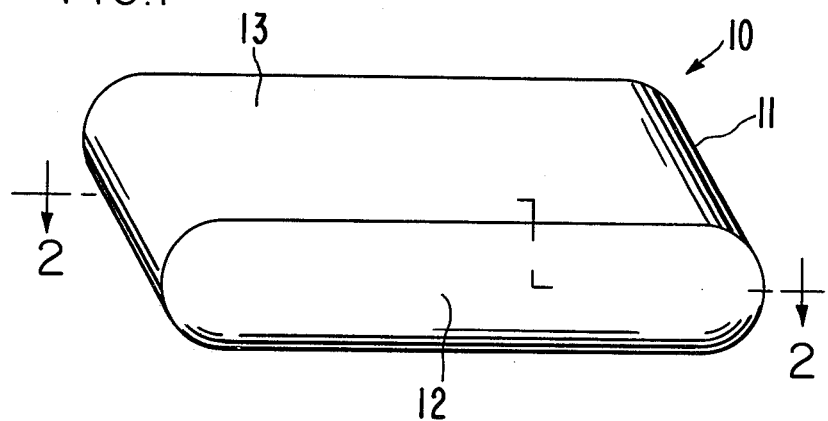
FIG. 1 is a view of an ocular insert made and used according to the invention.

Turning now to the drawings in detail, which are an example of a new and useful ocular insert for dispensing a medication formulation, and which example is not to be construed as limiting, one insert is indicated in FIG. 1 by numeral 10. System 10, as seen in FIG. 1, is an ocular therapeutic system manufactured for administering a medication formulation, not seen in FIG. 1, to the eye, particularly the eye of warm-blooded animals. System 10 comprises a body 11 made of a film consisting essentially of a single, solid polymer 12, and system 10 has at least one surface 13 for releasing formulation to the eye.

System 10 is manufactured as an insert or device, sized, shaped and adapted for easy insertion and comfortable retention in the eye. The system can have any geometric shape, and its dimensions can vary. The lower limit on the size of the system 10 is governed by the amount of medication formulation to be housed and administered to elicit the desired pharmacologic response, as well as the smallest sized system that can be conveniently inserted and maintained in the eye. The upper limit on the size of system 10 is governed by the space limitations of the eye, consistent with comfortable insertion and retention in the eye. Satisfactory results can be obtained with ocular systems having a length of 2 to 20 millimeters, a width of 1 to 15 millimeters, and a thickness of 0.1 to 7.5 millimeters. These systems can be inserted in the cul-de-sac of the eye of an adult human for prolonged, comfortable retention. Ocular system 10 is made of non-toxic, flexible materials that are nonallergenic to the eye, and it, 10, is designed for the eye of animals. The term animals includes warm-blooded mammals and humans.

Figure 2A:
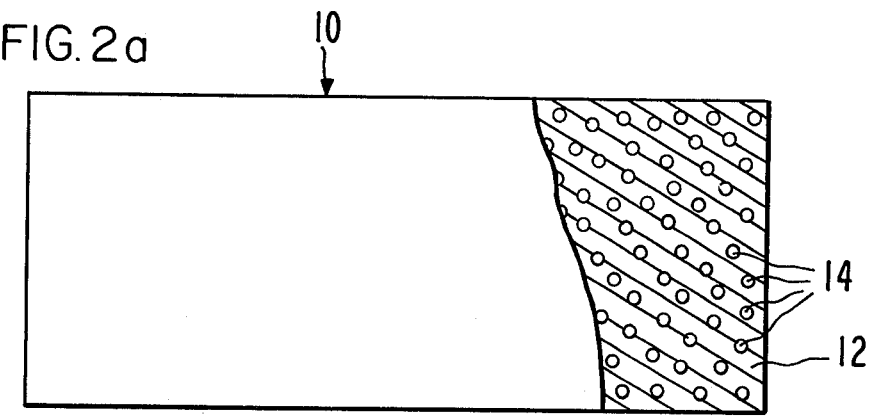
FIG. 2a is a cross-sectional view of the insert taken through 2—2 of FIG. 1 for illustrating the internal structure of the insert.
Figure 2B:
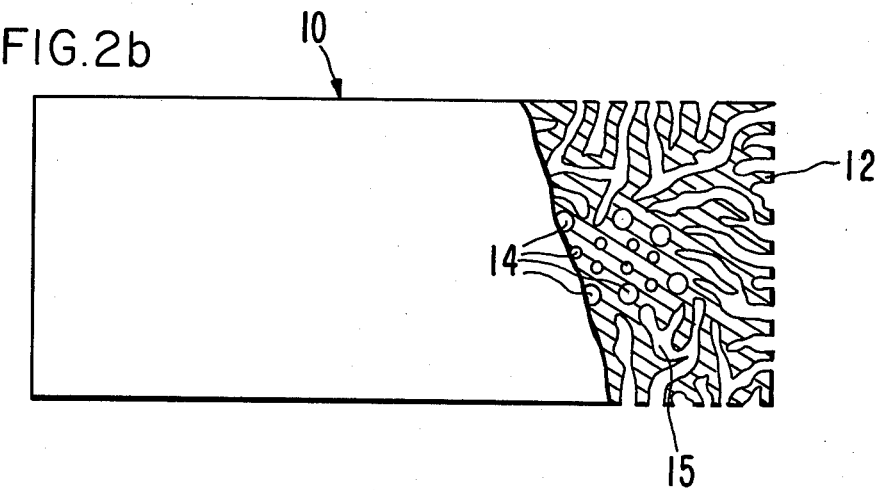
FIG. 2b is a cross-sectional view similar to the view of FIG. 2a which former figure illustrates the insert at a different period of use.

System 10 of FIG. 1 is seen in FIGS. 2a and 2b in cross-section through 2—2 of FIG. 1. In FIGS. 2a and 2b, insert 10 comprises a plurality of discret depots 14 of drug formulation dispersed through a polymer matrix 12. The polymer surrounds and encloses depots 14 and binds them into solid, unit body 11. Polymer 12 surrounds depots 14 individually so that each depot 14 is encapsulated by a layer of polymer 12. Polymer 12 is made of a material that is non-toxic, substantially non-erodible in the eye, impermeable to the passage of drug formulation, and it is permeable to the passage of an external fluid, that is, tear fluid. The drug formulation comprising depots 14 consists essentially of two structurally drugs, pilocarpine osmotically effective solute, and epinephrine osmotically effective solute.

In FIG. 2b system 10 is depicted in operation dispensing drug formulation over a prolonged period of time. In operation, when system 10 is in a fluid enviornment, the fluid diffuses into polymer 12 and is imbibed into depot 14 dissolving the drug formulation therein. The rate of fluid imbibition into depot 14 is related to the osmotic pressure gradient exhibited by the drug formulation of pilocarpine solute and epinephrine solute across the polymer encapsulating depot 14 against the external fluid. As fluid is imbibed into depot 14, it continuously dissolves the solutes and continuously fills depot 14, which solution thereby generates a hydrostatic pressure in depot 14. This pressure is applied against the polymer causing it to rupture and form an aperture. Drug formulation is then released through the aperture from depot 14 near the surface ofsystem 10 to the eye. Drug formulation is continuously released from system 10 by the inward progressive formation of apertures in depot 14, forming a lattice formulation dispensing paths in polymer 12 for releasing formulation from within the system 10 to its exterior. The dispensing paths can form openings on all sides of system 10, they can be interconnected through tortuous paths of regular and irregular shapes discernible by microscopic examination. As fluid is imbibed into depot 14, it fills the paths and it becomes a means for enhancing formulation transport therethrough, with release occuring at a controlled and beneficial rate over a prolonged period of time.

Figure 3:
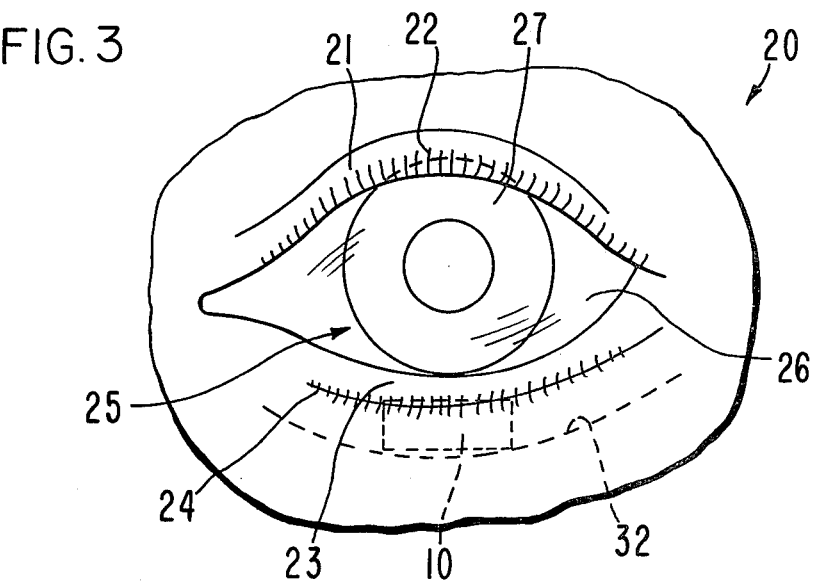
FIG. 3 is an illustration of the insert of FIG. 1 depicting the insert in operation dispensing a medication formulation to an eye; and, FIG. 4 is a bar graph illustrating the improved results provided by the invention.

Referring to FIG. 3, ocular therapeutic system 10 is shown in an eye 20 for administering drug formulation to eye 20. Eye 20 comprises an upper eyelid 21 with eyelashes 22 at the edge of eyelid 21, and a lower eyelid 23 with eyelashes 24 at the edge of eyelid 23. Eye 20 anatomically comprises an eyeball 25 covered for the greater part of its posterior area by sclera 26 and its central area by cornea 27. Eyelids 21 and 23 are lined with an epithelial membrane or palpebral conjucntiva, not shown in FIG. 3, and sclera 26 is lined with a bulbar conjunctiva, not shown in FIG. 3. The portion of palpebral conjunctiva which lines upper eyelid 21 and underlying portion of the bulbar conjuctiva define an upper cul-de-sac, not seen in FIG. 3. The portion of the palpebral conjunctiva that lines the lower eyelid 23 and the underlying portion of the bulbar conjunctiva defines a lower cul-de-sac, not seen in FIG. 3. System 10 may be shaped, sized and adapted for insertion and retention in any part of the eye, and in one of the presently preferred embodiments, system 10 is sized, shaped and adapted for insertion in the upper cul-de-sac. In FIG. 3, system 10 is seen in broken continuous lines in the lower cul-de-sac, generally held in position by the normal pressure of the eyelid.

DETAILED DESCRIPTION OF THE INVENTION

In accordance with the practice of this invention, it has now been surprisingly found that ocular therapeutic system 10 can be provided for dispensing medication formulation 18 consisting of two medicaments at controlled rates over time. The two medicaments that can be dispensed are pilocarpine osmotically effective solute and epinephrine osmotically effective solute. The phrase pilocarpine osmotically effective solute as used for the purpose denotes a solute that exhibits an osmotic pressure gradient across the polymer wall forming the depot against the external fluid. The phrase includes pilocarpine therapeutically acceptable salts, such as the inorganic acid addition salts, including the hydrochloride, nitrate, hydrobromide, hydroiodide, sulfate, sulfamate and phosphate, the organic acid addition salts such as maleate, acetate, bitartrate, citrate, oxalate, succinate, benzoate, tartrate, fumurate, malate, madelate, and ascorbate, and the quaternary salts such as n-butyl pilocarpinium iodide, isoamyl pilocarpinium iodide, hexyl pilocarpinium chloride and octyl pilocarpinium iodide. The phrase epinephrine osmotically effective solute embraces epinephrine therapeutically acceptable salts including the hydrochloride, hydrobromide, sulfate, sulfamate, phosphate, maleate, acetate, bitartrate, citrate, oxalate, succinate, benzoate, fumurate, malate, mandelate, ascorbate, and the like.

System 10 housing and release of the two medicaments, pilocarpine solute and epinephrine solute, according to the mode and the manner of the invention is unexpected, as the solutes are distinct and different in many parameters. The solutes embrace different molecular structures, solubilities, osmotic pressure gradients and physiological properties, yet system 10 can simultaneously release the solutes at controlled rates and in beneficial amounts over time. For example, pilocarpine nitrate has a solubility of 27 grams in 100 ml of water solution and it exhibits an osmotic pressure of 37 atmospheres, pilocarpine hydrochloride has a solubility of 80 grams in 100 ml of water solution and an osmotic pressure of 300 atmospheres, while epinephrine bitartrate has a solubility of 67 grams in 100 ml of water solution and osmotic pressure of 78.5 atmospheres, and epinephrine hydrochloride has a solubility of 80 grams in 100 ml of water solution and an osmotic pressure of 185 atmospheres. These properties indicate a pilocarpine solute and an epinephrine solute would be incompatible for housing and releasing at controlled rates, and in meaningful amounts from system 10, particularly since they exhibit different osmotic pressure gradients, they possess different rates of fluid imbibition, into depot 14, and they have different degrees of solubilization in fluid imbibed into depot 14. The invention unexpectedly found system 10 can be made with meaningful release therefrom. System 10 houses in depot 14 from about 1 to 40 weight percent of pilocarpine solute and from 1 to 25 weight percent of epinephrine solute, with the remaining weight percent of system 10 polymer 12. Genreally, the depots in system 10 comprise 2 to 50% by weight, with a preferred range of 5 to 40% by weight of the total weight of the system. The amount of pilocarpine solute released from system 10 will be about 1 to 100 micrograms per hour and the amount of epinephrine solute released from system 10 will be about 1 to 30 micrograms per hour. The concurrent, substantially zero order rate of release of these solutes is unexpected in the light of their diverse properties discussed herein. Generally, the pilocarpine solute and the epinephrine solute will have a particle size of about 0.1 to 100 microns, and a presently preferred particle size of about 0.5 to 20 microns. The osmotic delivery device consisting of sole drug solute of a specific particle size dispersed in a polymer is the invention of Michaels and Guillod as disclosed and claimed in copending U.S. Patent Application Ser. No. 855,605, filed on Nov. 29, 1977. This application and the copending application are both assigned to the Alza Corporation of Palo Alto, California.

Procedures for measuring the surface area average diameter of solutes are reported in *J.Am. Chem. Soc.,* Vol. 60, 309, 1938; *The Surface Chemistry of Solids,* by Gregg, Second Edition, 1961, published by Reinhold Corporation, New York; *Adsorption, Surface Area and Porosity,* by Gregg, et al., 1967, published by Academic Press, New York; *Physical Adsorption of Gases,* by Yound et al., 1962, published by Butterworth & Company, Ltd., London; and, *Fine Particles Measurements,* by Valla, 1959, published by Macmillan, N.Y.

The pilocarpine solute and epinephrine solute used as the pilocarpine therapeutically acceptable salts and the epinephrine therapeutically acceptable salts, used for the present purpose, are commercially available, they are disclosed in *Chem. Abstracts,* Vol. 41, 2158, 1941; ibid. 42, 1392, 8970 to 8971, and 2728 to 2729, 1948; ibid. 43, 1800, 1947, ibid. 44, 6586 and 10912, 1950; ibid. 5665, 1951; ibid. 46, 4569, 1952; ibid. 46, 6464 and 7586, 1952; ibid. 47, 4486 and 11662, 1953; and they can be prepared by methods known in the art in *J. Pharm. Sci.,* Vol. 50, 854 to 855, 1961; *Merck Index,* Eighth Edition, 411 to 833, 1968; and the reference cited therein. The osmotic pressure, ATM, of the above solutes can be measured in a commercially available osmometer that measures the vapor pressure difference between pure water and the solution containing a solute to be analyzed, and according to standard thermodynamic principles, the vapor pressure ratio is converted into osmotic pressure difference. An osmometer that can be used for the present measurements is identified as Model 302B Vapor Pressure Osmometer, manufactured by the Hewlett Packard Company, Avondale, Pa.

Materials suitable for manufacturing system 10 can be selected from naturally occurring and synthetic polymeric materials. These polymers are biologically compatible with the eye, they form body 11, they are the encapsulating layer of depot 14, they are substantially impermeable to the pasage of both pilocarpine solute and epinephrine solute, they are permeable to the passage of biological fluid and water, and form an aperture during operation of system 10 in the environment of use. Procedures for ascertaining the impermeability and the permeability of polymeric films are known to the art in *Proc. Roy. Sci. London,* Series A, Vol. 148, 1935; *J. Pharm. Sci.,* Vol. 55, 1224 to 1229, 1966; *Diffusion in Solids, Liquids and Gases,* by Jost, Chapter Xl, 436 to 488, 1960, published by Academic Press, Inc, N.Y. Procedures for measuring aperture formation resulting in system 10 by the hydrostatic pressure in depot 14 exceeding the cohesive integrity of the polymer with the polymer opening for releasing medication formulation to the environment of use, can be determined by measurements predicated on pressure-deflection and mechanical behavior measurements techniques reported in *Modern Plastics,* Vol. 41, 143 to 144, 146 and 182, 1964; *Handbook of Common Polymers,* by Scott et al., 588 to 609, 1971, published by CRC Press, Cleveland, Ohio; *Machine Design,* 107 to 111, 1975; *J. Sci. Instruments,* Vol. 42, 591 to 596, 1965; and by measuring mechanical stress-strain patterns of polymers using the Instron ® Testing Machine, available from Instron Coporation, Canton, Massachuesetts.

Exemplary materials for fabricating system 10 include ethylene-vinyl ester copolymers having an ester content of 4 to 80% such as ethylene-vinyl acetate copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3- dimethyl butanoate copolymer, and ethylene-vinyl benzoate copolymer. Ethylene-vinyl ester copolymers including ethylene-vinyl acetate copolymers for the manufacture of diffusional ocular drug delivery devices where the drug dissolves in and passes through the polymer by diffusion is the invention of Higuchi and Hussain as disclosed and claimed in U.S. Patent Application Ser. Nos. 705,470 and 705,479, both filed on July 15, 1976 and assigned to the Alza Corporation of Palo Alto, California. Solutes, as used for the present purpose in salt and ion states, do not substantially diffuse through polymer, as reported in *Biological Science, Molecules to Man*, By Welch et al., pages 157 and 158, 1968, published by Houghton Mifflin Company, Boston. Additional exemplary materials suitable for manufacturing system 10 include acrylonitrile-methyl vinyl ether, vinyl chloride-diethyl fumarate, homopolymers and copolymers of partially hydrolyzed poly(vinyl alcohol), plasticized poly(vinyl chloride), plasticized poly(amides), poly(isoprene), poly(isobutylene), poly(ethylene), lightly cross-linked poly(vinyl pyrrolidone), vinyl-diethyl fumarate copolymers, ethylene-propylene copolymers, poly(urethanes), poly(saccharides), and the like. The polymeric materials are known in *Handbook of Common Polymers*, by Scott, et al., Sections 1 through 42, 1971, published by CRC Press, Cleveland, Ohio.

DESCRIPTION OF EXAMPLES OF THE INVENTION

The following examples are merely illustrative of the present invention and they should not be considered as limiting the scope of the invention in any way, as these examples and equivalents thereof will become more apparent to those versed in the art in the light of the present disclosure, drawings, and the accompanying claims.

EXAMPLE 1

An ocular medication dispensing system 10 of elliptical shape and comprised of depots housing drug formulation is manufactured by first micronizing separately epinephrine succinate and pilocarpine sulfate and then blending them into the medication formulation. Next, the formulation is encapsulated as depots by slowly adding the formulation over a period of 5 to 10 minutes, with continuous milling, to a heated two-roll mill previously charged with copolymeric ethylene-ethyl acrylate. The depot forming procedure is repeated by remilling an appropriate number of times, with the depot-formulation in the copolymer removed from the mill, and then extruded into a film. Next, the film is die-cut to yield system 10 for releasing formulation to an ocular environment over time.

EXAMPLE 2

15 grams of micronized particles of epinephrine bitartrate having an average particle size of 40 microns, and 12.5 grams of micronized pilocarpine nitrate having a particle size of 40 microns are thoroughly mixed from about 5 to 10 minutes in an internal Banbury mixer to yield a medication formulation. Next, the formulation is fed over a 5 to 10 minute period to a two-roll mill previously charged with ethylene-vinyl acetate copolymer having a vinyl acetate content of 40%, and the milling continued for 5 to 10 minutes for encapsulating the formulation. Then, the milled product is passed through a four-roll calendar to form a film. Finally, the film is die-cut to form ocular inserts 13.5×5.8×0.5 mm that can simultaneously release 7 µg/hr of epinephrine bitartrate and 12.5 µg/hr of pilocarpine nitrate.

EXAMPLE 3

An ocular insert for releasing pilocarpine osmotic solute and epinephrine osmotic solute to the eye of an animal is prepared as follows: 50 parts of commercially available poly(olefin), 25 parts of commercially available freshly micronized pilocarpine osmotic solute of 35 micron size, and 25 parts of commercially available freshly micronized epinephrine osmotic solute of 30 micron size are compounded on a Brabender Plastograph ® with gentle heat for 7 to 14 minutes until the solutes are surrounded with poly(ethylene). The mass is removed from the machine and pressed at 15,000 psi into a film having a thickness of 2 mm. Then, rectangle inserts, 14×6 mm are die-cut from the film to yield a product useful for the management of ocular hypertension.

EXAMPLE 4

The procedure of Example 3 is repeated with conditions as stated except that the polymer in this example is ethylene-vinyl acetate-acrylic acid terpolymer consisting of 28% vinyl acetate, 1% acrylic acid and the balance ethylene. In this example, the product is removed from the internal mixer and passed through the cooled rolls of a 3×8 inch rubber mill to form a 0.8 mm thick film, with portions of the film compression molded between heated plattens of a hydraulic press to form 0.4 mm thick film. The film is dried and elliptical ocular devices are punched from the dry film.

EXAMPLE 5

To 75 grams of ethylene-vinyl acetate copolymer having a vinyl acetate content of 28% on a Brabender Plasticorder ® bowl equipped with roller blades, which copolymer is masticated for 2 to 4 minutes, is added 20 grams of pilocarpine nitrate having a solubility in water of 0.27 gm/ml at 37° C., an osmotic pressure of 37 ATM, and a particle size of 40 microns, and 7 grams of epinephrine bitartrate having a solubility of 670 mg/ml in water at 37° C., a particle size of 35 microns and an osmotic pressure of 78.5 ATM, and the three osmotic insert-forming members blended for 20 minutes at 40 rpm. Next, the contents of the bowl are removed, cut into 3 mm ×3 mm pieces with a multi-blade strip die and the strips fed to the hopper of an extruder. The pieces have a residence time of 5 minutes in the extruder with the screw of the extruder rotating at 20 rpm. A film is extruded through a 12 mil opening at the end of the extruder and punched into 13.5×5.8 mm inserts. The inserts have a rate of release of 40 micrograms per hour of pilocarpine nitrate and 3 micrograms per hour of epinephrine bitartrate.

EXAMPLE 6

The procedure of Example 5 is repeated with the amount of both solutes in the depots increased and the size of the ocular insert enlarged to yield (a) inserts that release 40 micrograms per hour of pilocarpine solute and 6 micrograms per hour of epinephrine solute, and (b) inserts that release 60 micrograms per hour of pilocarpine solute and 6 micrograms per hour of epinephrine solute, with both inserts releasing formulation over an extended 14 day period.

EXAMPLE 7

First, 72 grams of ethylene-vinyl acetate copolymer having a vinyl acetate content of 28% is added to a Banbury mixing bowl mounted on a Brabender preparation center and the copolymer allowed to masticate for five minutes, during this time the temperature rises to about 60° C. Next, a preweighed formulation of 19.0 grams of pilocarpine nitrate, USP, and 9.0 grams of epinephrine bitartrate, USP, is slowly added to the mixing bowl. After all the formulation is added to the internal mixing bowl, the formulation is encapsulated as depots by the copolymer over 15 minutes. Then, the contents of the bowl are removed and cut into small pieces and fed into the hopper of an extruder. The precut insert is extruded through the debuteuse at the end of the extruder into 0.7 mm film, at 75° C. Next, the elliptical shaped monolithic inserts are cut from the film, having dimesnions of 14×6 mm. These inserts release pilocarpine nitrate at the rate of 20 µg/hr, expressed as the free base, over a prolonged period of 8 days. The inserts exhibit a substantially zero order rate of release into a 0.9% saline at 37° C., measured spectrophometrically.

EXAMPLE 8

Prescisely 68 grams of ethylene-ethyl acrylate copolymer having an ethyl acrylate content of 18 mole percent, are added to the rolls of a two-roll rubber mill and worked until the polymer is well banded on the rolls. Next, 25 grams of pilocarpine hydrochloride, USP, are slowly added to the copolymer followed by 7 grams of epinephrine hydrochloride, USP, and the solutes encapsulated as depots in the copolymer. Then, the mill is stopped, the copolymeric formulation removed from the mill and comminuted by conventional means and extruded into 1.2 mm film at 80° C. Next, crescent shaped monolithic inserts are die-cut from the film having a length of 17 mm and a width of 6 mm. These monoliths release, expressed as the base, pilocarpine hydrochloride at the rate of 40 µg/hr and epinephrine hydrochloride at the rate of 9 µg/hr over a prolonged period of two weeks.

APPLICATION OF THE INVENTION

The ocular systems of this invention were evaluated for the effect of epinephrine osmotic solute delivered simultaneously with pilocarpine osmotic solute on the steady aqueous humor pilocarpine concentration. The study used three different systems that have a simultaneous rate of release of pilocarpine nitrate and epinehprine bitartrate, expressed as base, of 20 µg/hr and 1 µg/hr and 3 µg/hr; and 20 µg/hr and 6 µg/hr, respectively. The study compared the results obtained for the dual solute releasing system with the aqueous humor pilocarpine concentration produced by systems that release 20 µg/hr and 40 µg/hr of pilocarpine nitrate.

The studies used New Zealand white rabbits, either gender, 1.6 to 2.5 kg/body weight. The systems were inserted into the lower cul-de-sac of one rabbit eye, OD or OS. One eye was used for the study and the systems were left in the eye for two hours. At five minutes before sampling time, each rabbit was immobilized and anesthesized by intramuscular injections. The eye was then proptosed, and an aqueous humor sample withdrawn from the anterior chamber by a 1 cc tuberculin syringe equipped with a 30 gauge needle. The samples were analyzed by the method of Bayne, et al., *J. Pharm. Sci.*, Vol. 64, pages 402 to 404, 1975. The standards used in the assay were 500 pg, 1.0, 2.0 and 4.0 ng pilocarpine, and methazolamide was used as the internal standard. The heptafluoroabutyric derivatives or pilocarpine were detected by electron capture gas chromatography using a Varian Aerograph ®, on a Chromsorb ® column at 195° C.

Figure 4:
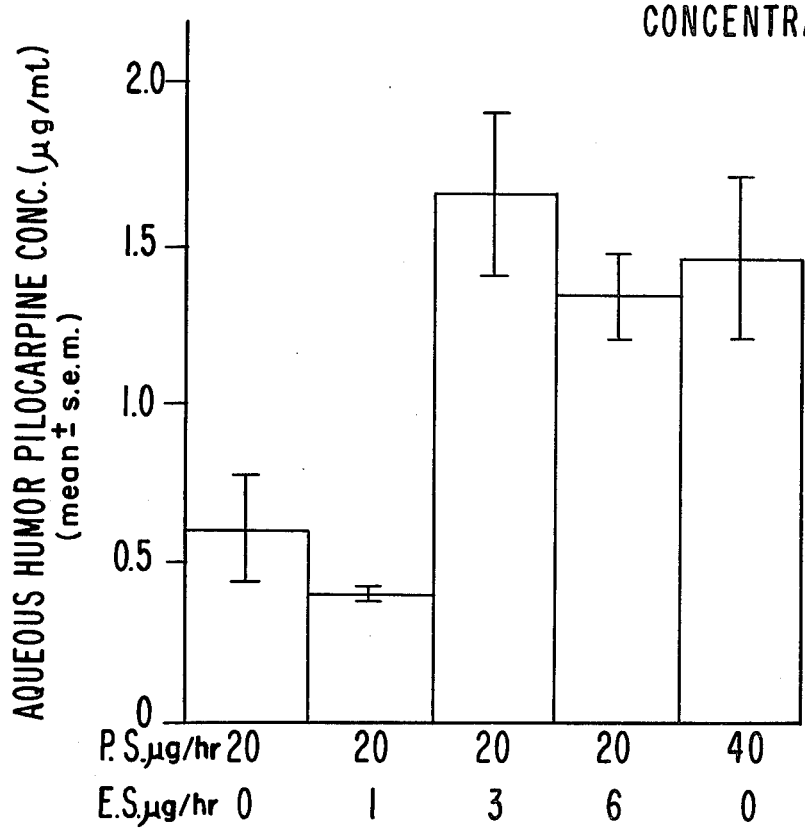

The aqueous humor pilocarpine concentrations in each group were averaged. A non-parametric statistic, the Wilcoxin-Mann-Whitnes tests, were used for comparing the expermimental groups. The data obtained is summarized in FIG. 4. The results show the simultaneous delivery of epinephrine solute with pilocarpine solute producing a statistically significant enhancement of pilocarpine aqueous humor levels. In FIG. 4, n equals the number of animals, and s.e.m. denotes the standard error of the means. The system had a surface area per system side of 0.67 cm$^2$. The letters P.S. µg/hr indicates release of pilocarpine solute in µg/hr, and E.S. indicates release of epinephrine solute in µg/hr.

The systems of the invention can be used for the management of intraocular pressure associated with glaucoma. The systems are useful for treating primary glaucoma including narrow-angle or acute, and wide-angle or chronic simple glaucoma, secondary glaucoma, and preoperatively in acute-angle closure where a delay of surgery is desired in order to lower intra-ocular tension. Glaucoma and its biological effects in humans, and pilocarpine and its course of action, are described in *The Pharmacological Basis of Therapeutics*, 4th Edition, by Goodman and Gilman, pages 458 to 460, 1970, published by the Macmillan Company, New York, and in *General Ophthalmolgy*, by Vaughn and Asbury, pages 192 to 209, 1974, published by Lange Medical Publications, Los Altos, California. The metabolic history of epinephrine and the action of catechol methyltransferase and monoamine oxidase on epinephrine are described in Chapter 24 of Goodman and Gilman.

While specific considerations, examples and disclosures have been described and discussed herein, such have been offered solely to exemplify the present invention, and they should not be considered as limiting the scope and the nature of the invention.

We claim:

1. An ocular therapeutic system for dispensing a medication formulation to an eye, said system sized, shaped and adapted for easy insertion and comfortable retention in the eye and comprising, depots of a medication formulation consisting essentially of from 1 to 40 weight percent of a pilocarpine therapeutically acceptable salt of 0.1 to 100 micron size and 1 to 25 weight percent of an epinephrine therapeutically acceptable salt of 0.1 to 100 micron size, said depots dispersed in and surrounded substantially individually by a polymer that is impermeable to the passage of the medication formulation and permeable to the passage of eye fluid.

2. The ocular therapeutic system for dispensing the medication formulation according to claim 1, wherein the pilocarpine salt and the epinephrine salt are selected from the group consisting of inoganic acid addition salts, organic acid addition salts and quaternary addition salts.

3. The ocular therapeutic system for dispensing the medication formulation according to claim 1, wherein the pilocarpine therapeutically acceptable salt and the epinephrine therapeutically acceptable salt are selected from the group of salts consisting essentially of hydrochloride, nitrite, hydrobromide, hydroiodide, sulfate, sulfamate, phosphate, nitrate, acetate, bitartrate, citrate, oxalate, succinate, benzoate, tartrate, fumurate, malate, mandelate, maleate and ascorbate.

4. The ocular therapeutic system for dispensing the medication formulation according to claim 1, wherein the system is manufactured as an insert for insertion and retention in a human eye, and the depots comprise 2 to 50% by weight of the insert.

5. An ocular insert consisting essentially of (a) discrete depots of a medication formulation of a pilocarpine osmotically effective solute and an epinephrine osmotically effective solute, which solutes have a size of 0.1 to 100 microns and exhibit an osmotic pressure gradient across the wall of the depot against an external fluid present in the environment of use; (b) a film of an ethylene-vinyl ester copolymer forming the insert, imparting size and shape to the insert for easy insertion and prolonged retention in the environment of use, said film substantially impermeable to the passage of the solutes, permeable to the passage of the external fluid and substantially surrounding individually and serving as the wall of the depots; and, (c) wherein, when the insert is positioned in the environment of use, fluid from the environment is imbibed through the wall into the depots to continuously dissolve the solutes and generate a hydrostatic pressure in the depots which pressure is applied against the wall of the depots thereby forming apertures and releasing the formulation from the depots at the surface and from within the insert by the inward progressive aperture formation in depots at a controlled rate over a prolonged period of time.

6. The ocular insert according to claim 5, wherein the ester is the acetate, the pilocarpine solute is the nitrate, the epinephrine solute is the bitartrate, the depots house from 1 to 40 weight percent of the nitrate, and from 1 to 20 weight percent of the bitartrate, and the environment is the human eye.

7. A method for treating glaucoma in a warm-blooded animal, which method consists essentially in lowering the intraocular pressure associated with glaucoma by administering to the eye of the animal a medication formulation, the method consisting essentially in the steps of:

(a) positioning in the eye an ocular insert, said insert consisting essentially of:
  (1) discrete depots of a medication formulation consisting of a pilocarpine osmotic solute and an epinephrine osmotic solute, which solutes exhibit osmotic pressure gradients across the wall of the depot against an external fluid, said depots dispersed in;
  (2) a film sized and shaped as an insert for easy positioning and retention in the eye of the animal, said film a polymeric material that surrounds individually and forms the wall of the discret depots, is non-toxic, nonerodible, impermeable to the passage of the solutes and permeable to the passage of fluid;
(b) imbibing fluid from the eye into the depots to dissolve the solutes and fill the depots with solution, thereby exerting pressure aganst the wall of the depot and forming apertures that release formulation from the depots at the surface and from the interior of the insert through formulation dispensing paths made by the inward progressive aperture formation in related depots; thereby,
(c) administering formulation to the eye at a controlled rate for treating glaucoma over a prolonged period of time.

8. The method for treating glaucoma in a warm-blooded animal according to claim 7, wherein the glaucoma is wide-angle glaucoma, the polymeric material is ethylene-vinyl acetate copolymer, and the animal is human.

9. The method for treating glaucoma in a warm-blooded animal according to claim 7, wherein the glaucoma is secondary glaucoma, the polymeric material is ethylene-vinyl acetate copolymer, and the animal is a human.

10. The method for treating glaucoma in a warm-blooded animal according to claim 7, wherein the insert administers simultaneously from 1 to 100 micrograms per hour of pilocarpine solute and from 1 to 30 micrograms per hour of epinephrine solute.

11. The method for treating glaucoma in a warm-blooded animal according to claim 7, wherein pilocarpine solute is pilocarpine nitrate and epinephrine solute is epinephrine bitartrate.

* * * * *